United States Patent
Klumb et al.

[11] Patent Number: 5,935,124
[45] Date of Patent: Aug. 10, 1999

[54] TIP ELECTRODE WITH MULTIPLE TEMPERATURE SENSORS

[75] Inventors: Katherine Klumb, Los Altos; Kristine Fuimaono, Covina, both of Calif.

[73] Assignee: Cordis Webster, Inc., Baldwin Park, Calif.

[21] Appl. No.: 08/982,667

[22] Filed: Dec. 2, 1997

[51] Int. Cl.⁶ .................................................. A61B 17/39
[52] U.S. Cl. .......................... 606/42; 606/31; 606/45; 607/102
[58] Field of Search .................... 606/27–31, 41, 606/42, 45–50; 607/100–102, 104, 105, 115, 116, 122; 600/374

[56] References Cited

U.S. PATENT DOCUMENTS

| | | |
|---|---|---|
| Re. 34,502 | 1/1994 | Webster, Jr. . |
| 5,122,137 | 6/1992 | Lennox ..................................... 606/40 |
| 5,423,805 | 6/1995 | Brucker et al. . |
| 5,456,682 | 10/1995 | Edwards et al. .......................... 606/31 |
| 5,715,817 | 2/1998 | Stevens-Wright et al. ............. 600/374 |
| 5,718,701 | 2/1998 | Shai et al. ................................. 606/41 |
| 5,807,249 | 9/1998 | Qin et al. ................................ 600/374 |
| 5,827,278 | 10/1998 | Webster, Jr. .............................. 606/41 |
| 5,843,076 | 12/1998 | Webster, Jr. et al. ..................... 606/41 |
| 5,853,409 | 12/1998 | Swanson et al. .......................... 606/31 |

*Primary Examiner*—Michael Peffley
*Attorney, Agent, or Firm*—Christie, Parker & Hale, LLP

[57] ABSTRACT

A catheter comprises a catheter body, a tip section, and a control handle. The catheter body has proximal and distal ends and at least one lumen extending therethrough. The control handle is located at the proximal end of the catheter body. The tip section has proximal and distal ends and at least one lumen therethrough, with the proximal end of the tip section being fixedly attached to the distal end of the catheter body. A tip electrode is fixedly attached at the distal end of the tip section. The tip electrode has a blind hole extending therethrough. A wire, preferably a puller wire, extends and is fixedly attached into the blind hole of the tip electrode. At least two temperature sensors are fixedly attached along the length of the wire within the blind hole.

27 Claims, 7 Drawing Sheets

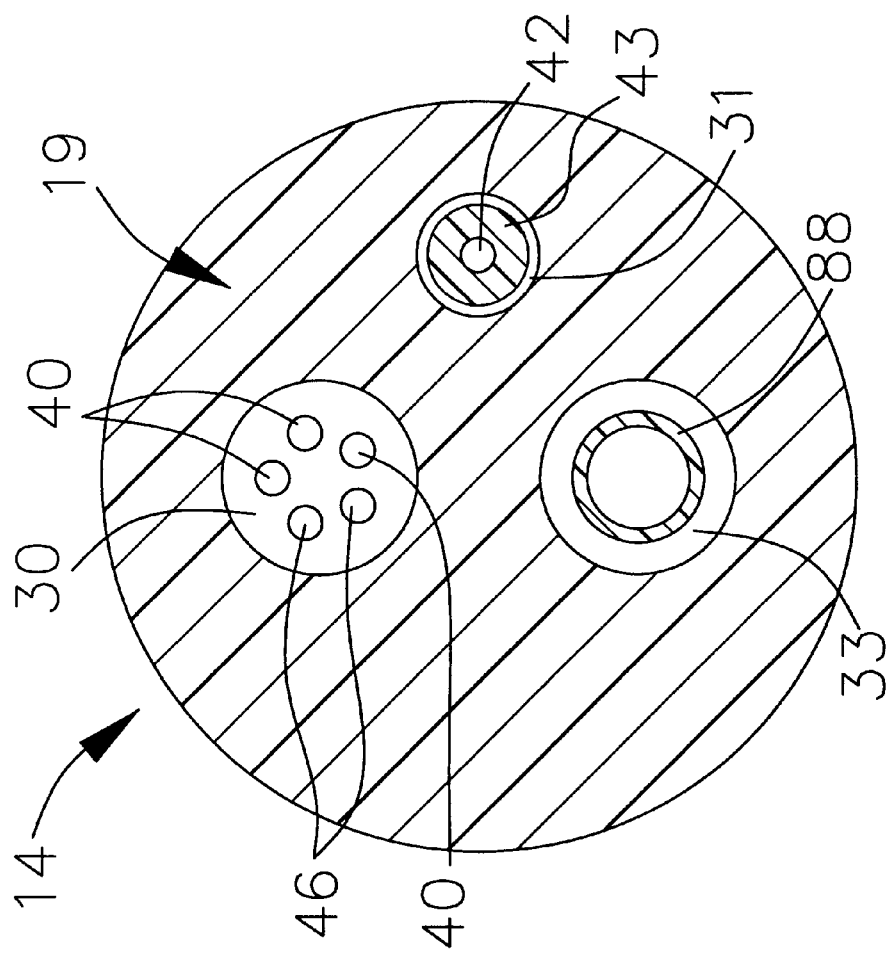

TIP ELECTRODE WITH MULTIPLE TEMPERATURE SENSORS

FIELD OF THE INVENTION

The present invention relates to an ablation catheter having a tip electrode containing multiple temperature sensors at predetermined locations within the tip electrode.

BACKGROUND OF THE INVENTION

Ablation catheters typically have a tip electrode at their distal end for ablating the heart tissue. Temperature sensors are used to monitor the temperature of the tip electrode in contact with the heart tissue to assist the physician in determining whether the tip electrode is too hot. When the tip electrode becomes too hot, coagulation forms on the tip electrode, causing a steam explosion in the heart tissue. Typical tip electrodes have a length of approximately 4 mm. In certain applications, e.g., when longer lesions are desired, longer tip electrodes are preferred. When longer tip electrodes are used, e.g., around 8 mm to 12 mm, accurately determining the temperature of the electrode in contact with the heart tissue becomes more difficult. This is because the temperature of the tip electrode will vary across its surface, e.g., depending on whether the surface is in contact with myocardium or circulating blood. Consequently, if a single temperature sensor is used, it may be at a location within the tip electrode remote from the portion of the tip electrode in contact with the heart tissue. If that sensor is adjacent a portion of the tip electrode in contact with rapidly circulating blood, it may provide a temperature reading which is not indicative of the portion of the tip electrode that is in contact with the heart tissue. Thus, it is desirable to place multiple temperature sensors along the length of the tip electrode to more accurately monitor the temperature of the portion of the tip electrode in contact with the heart tissue.

Preferably, the temperature sensor will be as close as possible to the surface of the tip electrode in contact with the heart tissue. However, placement of a temperature sensor on one side of the tip electrode will provide erroneous temperature readings if the opposite side of the electrode is in contact with the heart tissue. Therefore, it is generally preferred that temperature sensors be located along the axis of the tip electrode.

The temperature of the tip electrode is typically controlled by an RF generator having a feedback control circuit. The generator receives signals from the temperature sensor and supplies more or less RF energy to the tip electrode depending on the signal received. When multiple temperature sensors are used, the generator uses as a control the temperature sensor measuring the fastest temperature change.

To take advantage of multiple temperature sensors, it is desirable to know the distance between the sensors within the tip electrode. This allows the physician to have a general idea of the region of the tip electrode that each sensor is measuring. However, it is difficult to place multiple sensors within the tip electrode at known locations. Typically, temperature sensors are soldered or glued directly into holes within the tip electrode. Because of the size of the components, it is difficult to attach a temperature sensor within a hole at a particular location using this traditional method. Thus, a need exists for a catheter having multiple temperature sensors within the tip electrode situated at predetermined spaced-apart locations.

SUMMARY OF THE INVENTION

The present invention provides a steerable catheter particularly useful in ablation procedures having at least two temperature sensors within a tip electrode at predetermined, spaced-apart locations, preferably along the axis of the tip electrode. The catheter comprises a catheter body, a tip section attached to the distal end of the catheter body and a control handle attached to the proximal end of the catheter body. The tip section has at least one lumen and a tip electrode fixedly attached at its distal end. The tip electrode has a blind hole, preferably a blind axial hole, extending along a portion of its length in communication with the lumen in the tip section. An anchor wire extends into the blind hole of the tip electrode and carries at least two temperature sensors fixedly attached along its length. The temperature sensors are fixedly attached at predetermined, spaced-apart locations along the length of the anchor wire so that the physician knows their location and the distance between them.

Preferred temperature sensors are thermocouples. A particularly preferred thermocouples comprises a double-stranded enameled wire pair comprising a copper wire, e.g., a number 40 copper wire, and a construction wire, e.g., a constantan wire, which gives support and strength to the wire pair. At the wires' distal ends, the enamel is removed, and the wires are twisted and welded to the anchor wire. The wires are connected at their proximal ends to a temperature monitor.

In a preferred embodiment of the invention, the anchor wire is also used as a puller wire. Such a puller wire is attached at its proximal end to the control handle and extends through a lumen in the catheter body and an off-axis lumen in the tip section to the tip electrode. Manipulation of the control handle results in lengthwise movement of the puller wire relative to the catheter body and deflection of the tip section.

In a particularly preferred embodiment of the invention, the puller wire comprises a ferrule fixedly attached at its distal end. Multiple temperature sensors are fixedly attached at designated locations along the length of the ferrule, which is soldered or otherwise fixedly attached inside the blind hole in the tip electrode.

In another preferred embodiment the catheter contains an infusion tube for infusing fluids into the heart tissue, for example, to cool the tip electrode. The infusion tube extends through the catheter body, into a lumen in the tip section and into a passage into the tip electrode. The passage in the tip electrode allows fluid to flow from the infusion tube through the tip electrode and into the heart. The proximal end of the infusion tube terminates in a luer hub or the like. Alternatively, a first infusion tube extends through the catheter body and into the proximal end of a lumen in the tip section. A second infusion tube extends from the distal end of the same tip lumen to a passage extending through the tip electrode.

DESCRIPTION OF THE DRAWINGS

These and other features and advantages of the present invention will be better understood by reference to the following detailed description when considered in conjunction with the accompanying drawings wherein:

FIG. 10 is a transverse cross-sectional view of the tip section of FIG. 9 across line 10—10.

DETAILED DESCRIPTION

A particularly preferred catheter constructed in accordance with the present invention is shown in FIGS. 1 to 4. The catheter 10 comprises an elongated catheter body 12 having proximal and distal ends, a deflectable tip section 14 at the distal end of the catheter body 12, and a control handle 16 at the proximal end of the catheter body 12

Figure 1:
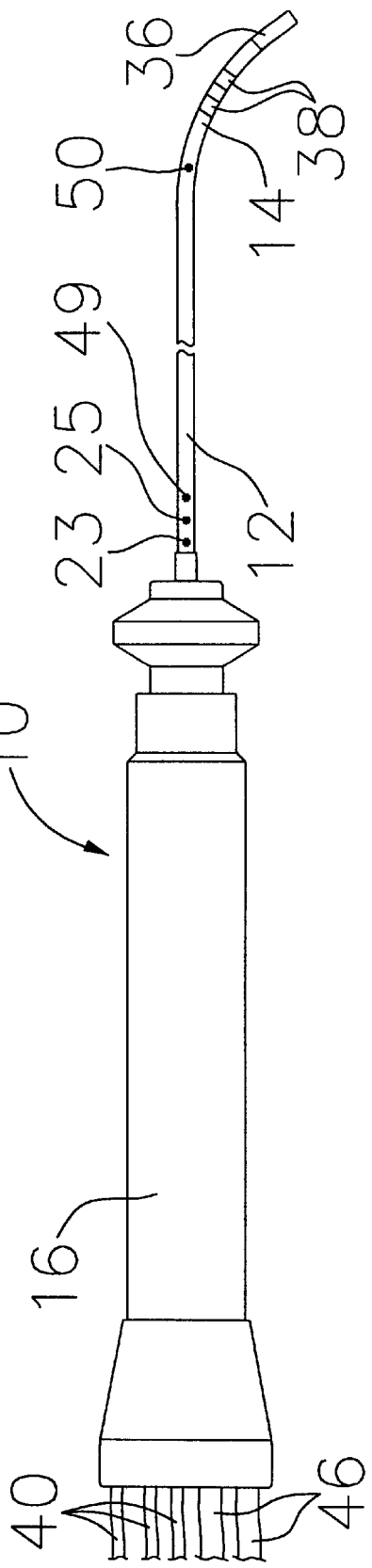
FIG. 1 is a side cross-sectional view of an embodiment of the catheter of the invention.
Figure 2:
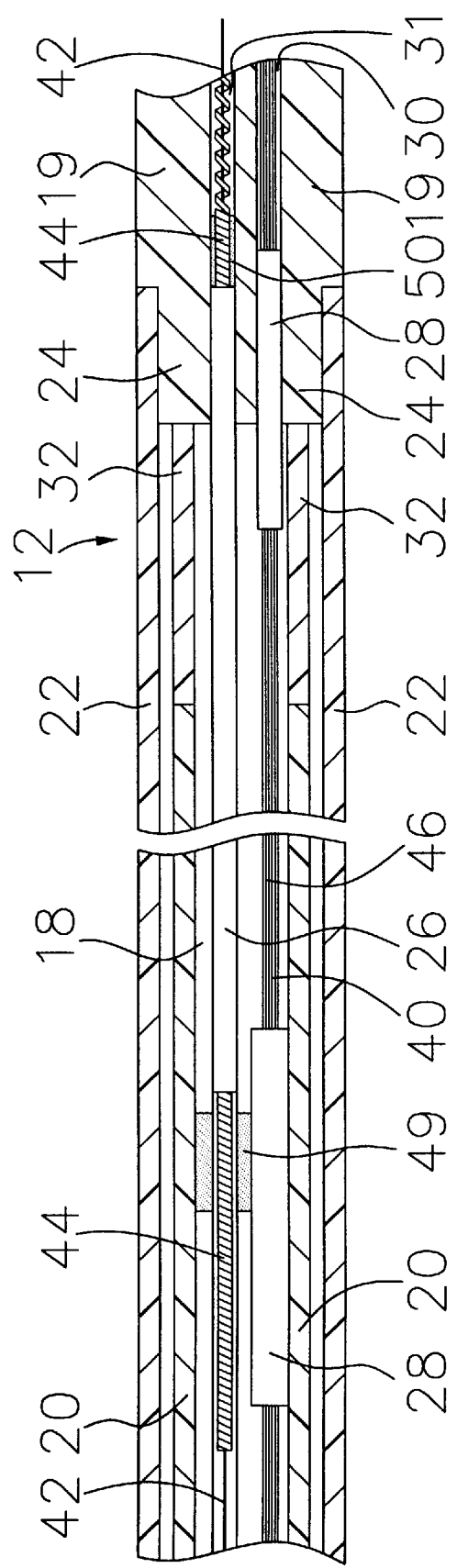
FIG. 2 is a side cross-sectional view of the catheter body, including the junction between the catheter body and the tip section.

With reference to FIG. 2, the catheter body 12 comprises an elongated tubular construction having a single, central lumen 18. The catheter body 12 is flexible, i.e., bendable, but substantially non-compressible along its length. The catheter body 12 can be of any suitable construction and made of any suitable material. A presently preferred construction comprises an outer wall 22 made of polyurethane or nylon. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner. The outer diameter of the catheter body 12 is not critical, but is preferably no more than about 8 french. Likewise the thickness of the outer wall 22 is not critical.

The inner surface of the outer wall 22 is lined with a stiffening tube 20, which can be made of any suitable material, preferably polyimide. The stiffening tube 20, along with the braided outer wall 22, provides improved torsional stability while at the same time minimizing the wall thickness of the catheter body 12, thus maximizing the diameter of the central lumen 18. The outer diameter of the stiffening tube 20 is about the same as or slightly smaller than the inner diameter of the outer wall 22. Polyimide tubing is presently preferred because it may be very thin walled while still providing very good stiffness.

A particularly preferred catheter has an outer wall 22 with an outer diameter of about 0.091 inch and an inner diameter of about 0.063 inch and a stiffening tube 20 having an outer diameter of about 0.60 inch and an inner diameter of about 0.037 inch.

Figure 3:
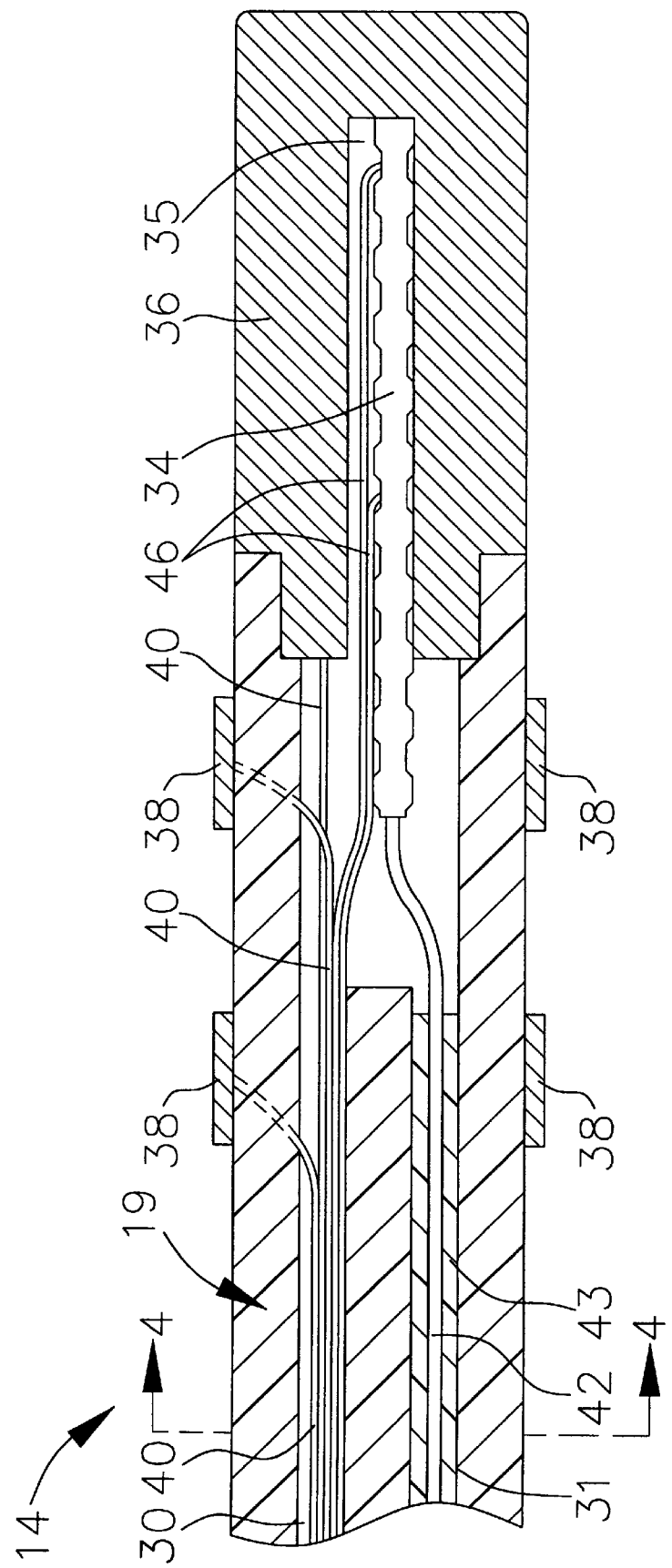
FIG. 3 is a side cross-sectional view of the catheter tip section showing an embodiment having two lumens where the puller wire is anchored in the tip electrode.
Figure 4:
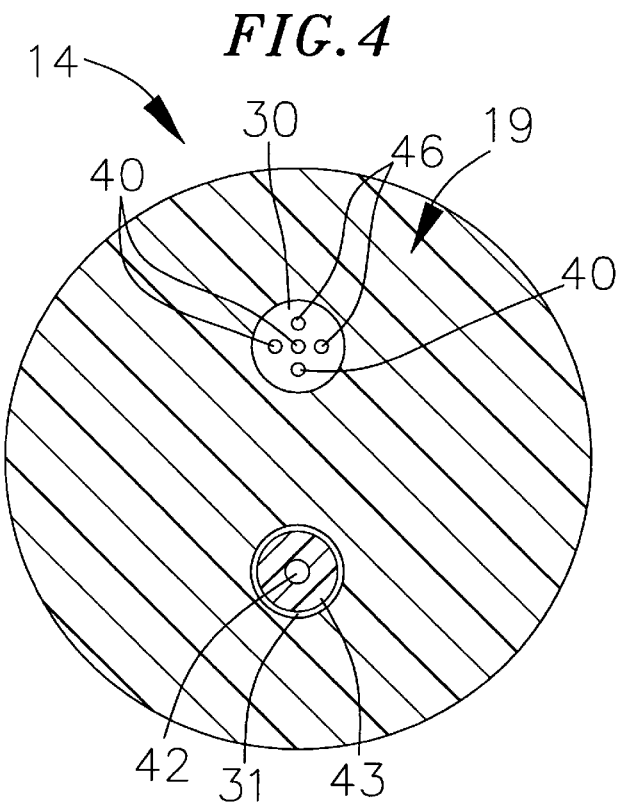
FIG. 4 is a transverse cross-sectional view of the tip section of FIG. 3 along line 4—4.

As shown in FIGS. 3 and 4, the tip section 14 comprises a short section of tubing 19 having two off-axis tip lumens 30 and 31. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french. The sizes of the tip lumens 30 and 31 are not critical. In a particularly preferred embodiment, the tip section 14 has an outer diameter of about 7 french (0.092 inch) and the two tip lumens 30 and 31 are generally about the same size, each having a diameter of about 0.20 inch.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. In the arrangement shown, a spacer 32 lies within the catheter body 12 between the distal end of the stiffening tube 20 and the proximal end of the tip section 14. The spacer 32 is preferably made of a material that is stiffer than the material of the tip section 14, e.g., polyurethane, but not as stiff as the material of the stiffening tube 20, e.g., polyimide. A spacer 32 made of Teflon® is presently preferred. A preferred spacer 32 has a length of from about 0.25 inch to about 0.75 inch, more preferably about 0.5 inch. Preferably the spacer 32 has an outer and inner diameter about the same as the outer and inner diameters of the stiffening tube 20. The spacer 32 provides a transition in flexibility at the junction of the catheter body 12 and catheter tip 14, allowing the junction of the catheter body 12 and tip section 14 to bend smoothly without folding or kinking.

The spacer 32 is held in place by the stiffening tube 20. The stiffening tube 20, in turn, is held in place relative to the outer wall 22 by glue joints 23 and 25 at the proximal end of the catheter body 12. In a preferred construction of the catheter body 12, a force is applied to the proximal end of the stiffening tube 20, causing the distal end of the stiffening tube 20 to firmly butt up against and compress the spacer 32. While under compression, a first glue joint 23 is made between the stiffening tube 20 and the outer wall 22 by a fast drying glue, e.g. Super Glue®. Thereafter a second glue joint 25 is formed between the proximal ends of the stiffening tube 20 and outer wall 22 using a slower drying but stronger glue, e.g., polyurethane.

With reference to FIG. 3, at the distal end of the tip section 14 is a tip electrode 36. The proximal end of the tip electrode 36 has a circumferential notch 37 that fits inside the distal end of the tip section 14. The proximal end of the tip electrode 36 is bonded to the tip section 14 by polyurethane glue or the like.

The tip electrode 36 has a generally cylindrical shape with a rounded distal end, but may have any shape as desired as is well-known in the art. Preferably the tip electrode 36 has a diameter about the same as the outer diameter of the tubing 19. The tip electrode 36 has an exposed length, i.e., outside the plastic tubing 19 of the tip section 14, preferably of from about 3 mm to about 12 mm, more preferably of from about 6 mm to about 10 mm, still more preferably of about 8 mm.

The tip electrode 36 is generally solid with a blind hole 35 extending from its proximal end through most of its length. Preferably the blind hole 35 extends though at least about 50 percent of the length of the tip electrode, and more preferably at least about 85 percent of the length of the tip electrode. The diameter of the blind hole 35 preferably ranges from about 0.015 inch to about 0.30 inch. Preferably the blind hole 35 extends along the axis of the tip electrode 36, but can extend off-axis if desired.

In the embodiment shown in FIGS. 1 to 4, the tip section 14 carries one or more ring electrodes 38. The length of each ring electrode 38 is not critical, but is preferably about 1 mm to about 4 mm. The ring electrodes 38 are spaced apart a distance of about 2 mm to about 4 mm.

The tip electrode 36 and ring electrodes 38 are each connected to a separate lead wire 40. The lead wires 40 extend through the first tip lumen 30 of tip section 14, the central lumen 18 of the catheter body 12, and the control handle 16, and terminate at their proximal end in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath (not shown).

The lead wires 40 are attached to the tip electrode 36 and ring electrodes 38 by any conventional technique. Connection of a lead wire 40 to the tip electrode 36 is preferably accomplished by weld or the like, with the lead wire 40 wrapped around the proximal end of the tip electrode 36 within the plastic tubing 19.

Connection of a lead wire 40 to a ring electrode 38 is preferably accomplished by first making a small hole through the tubing 19 of the tip section 14. Such a hole can be created, for example, by inserting a needle through the tubing 19 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

A puller wire extends through the central lumen 18 in the catheter body 12. The puller wire is anchored at its proximal end to the control handle 16 and anchored at its distal end in the tip section 14. The puller wire comprises an elongated wire 42 and a ferrule 34 at the distal end of the wire 42. The wire 42 is made of any suitable metal, such as stainless steel or Nitinol, and is preferably coated with Teflon® or the like. The coating imparts lubricity to the wire 42. The wire 42 preferably has a diameter of from about 0.006 inch to about 0.010 inch.

The wire 42 extends into the second tip lumen 31 and is anchored in the blind hole 35 of the tip electrode 36. Withing the second tip lumen 31, the wire 42 extends through a plastic, preferably Teflon®, sheath 43, which prevents the wire 42 from cutting into the tubing 19 of the tip section 14 when the tip section is deflected.

The ferrule 34 adds thickness to the distal end of the puller wire, providing more surface area for the puller wire to be soldered into the blind hole 35 of the tip electrode 36. Preferably the ferrule 34 is made of stainless steel, but can also be made of any other suitable metal, ceramic or plastic. When made of metal, the ferrule 34 is preferably crimped on the wire 42. The distal end of the puller wire, including ferrule 34, preferably has an outer diameter ranging from about 0.020 inch to about 0.027 inch, more preferably about 0.022 inch. Preferably the ferrule 34 has a length slightly longer (e.g., about 1 to 2 mm) than the length of the blind hole 35 in the tip electrode 36 so that the proximal end of the ferrule extends into the tubing 19 of the tip section 14.

At least two temperature sensors are provided for the tip electrode 36 and are situated within the blind hole 35 of the tip electrode 36. A preferred temperature sensor comprises a thermocouple 46, but other temperature sensors, such as thermistors, could also be used. A preferred thermocouple is formed by a double-stranded enameled wire pair. One wire of the wire pair is a copper wire , e.g., a number 40 copper wire. The other wire of the wire pair is a constantan wire, which gives support and strength to the wire pair. The wires of the wire pair are electrically isolated from each other except at their distal ends where they contact the tip electrode 36. Any other suitable thermocouple could also be used, for example, a wire pair comprising a nickel chromium wire and a chromium copper wire. A suitable thermistor for use with the present invention is Model No. AB6N2-GC14KA143E/37C sold by Thermometrics (New Jersey).

The distal end of the wire pair of each thermocouple 46 is welded or otherwise fixedly attached, e.g., with solder or glue, to the ferrule 34 of the puller wire 42. Preferably one thermocouple 46a is anchored at the distal end of the ferrule 34 while the other thermocouple 46b is anchored near the midpoint of the ferrule 34. Preferably the distance between the thermocouples 46 is between about 40 percent and 60 percent of the length of the blind hole 35 in the tip section 36, more preferably about 50 percent of the length of the blind hole 35.

The distal end of the puller wire 42 containing the ferrule 34 and thermocouples 46 is soldered into the blind hole 35 in the tip section 36. Preferably the tip electrode 36 is heated and the distal end of the puller wire 42 containing the ferrule 34 is placed inside the blind hole 35. Solder is wicked into the blind hole 35 until full, then the tip electrode 36 is taken off the heat source. Preferably the entire blind hole 35 is filled with solder.

The wires pairs of the thermocouples 46 extend out the blind hole 35 of the tip electrode 36 and into the first tip lumen 30, through the central lumen 18 of the catheter body 12, through the catheter handle 16 and to a connector (not shown) connectable to a temperature monitor (not shown).

When more than two thermocouples 46 are mounted on the distal end of the puller wire, they are preferably equally spaced, i.e., mounted approximately equal distances from each other. For example, when the exposed section of the tip electrode 36 is 8 mm, the distance between the thermocouples 46 on the distal end of the puller wire is approximately 4 mm. Preferably, one thermocouple 46 is fixedly attached at or near the distal end of the ferrule 34.

A compression coil 44 extends from the proximal end of the catheter body 12 to the proximal end of the tip section 14 in surrounding relation to the puller wire 42. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. The plastic coating on the puller wire 42 allows it to slide freely within the compression coil 44. Along much of its length, the outer surface of the compression coil 44 is covered by a flexible, non-conductive sheath 26 to prevent contact between the compression coil 44 and the lead wires 40 within the central lumen 18 of the catheter body 12. A non-conductive sheath 26 made of polyimide tubing is presently preferred.

The compression coil 44 is anchored at its proximal end to the proximal end of the stiffening tube 20 in the catheter body 12 by a glue joint 49 and at its distal end to the tip section 14 at a location distal to the spacer 32 by a glue joint 50. Both glue joints 49 and 50 preferably comprise polyurethane glue or the like. The glue may be applied by means of a syringe or the like through a hole made between the outer surface of the catheter body 12 and the single lumen 18. Such a hole may be formed, for example, by a needle or the like that punctures the outer wall 18 of the catheter body 12 and the stiffening tube 20 and that is heated sufficiently to form a permanent hole. The glue is then introduced through the hole to the outer surface of the compression coil 44 and wicks around the outer circumference to form a glue joint about the entire circumference of the compression coil 44.

Alternatively, the compression coil 44 can be anchored at its distal end to the distal end of the catheter body 12. When a stiffening tube 20 is not used, the compression coil 44 can be anchored directly to the outer wall 22 of the catheter body 12.

The electrode lead wires 40 and thermocouples 46 must be allowed some longitudinal movement within the catheter body 12 so that they do not break when the tip section 14 is deflected. To provide for such lengthwise movement, there are provided tunnels through the glue joints 49 and 50, through which the lead wires 40 and thermocouples 46 extend to avoid contact with the glue. The tunnels are formed by transfer tubes 28, preferably made of short segments of polyimide tubing. Each transfer tube is approximately 60 mm long and has an outer diameter of about 0.021 inch and an inner diameter of about 0.019 inch.

Longitudinal movement of the puller wire 42 relative to the catheter body 12, which results in deflection of the tip section 14, is accomplished by suitable manipulation of the control handle 16. Any suitable steerable catheter handle can be used, for example, the handle described in U.S. Pat. No. 4,960,134, the disclosure of which is incorporated herein by reference.

Figure 5:
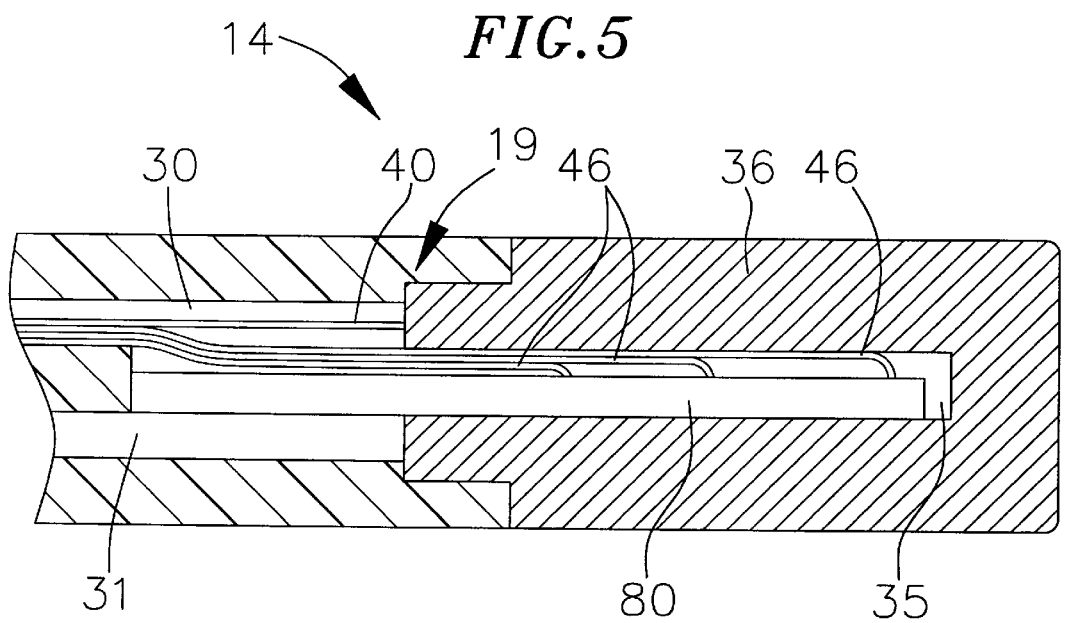
FIG. 5 is a side cross-sectional view of an alternative embodiment of the catheter tip section where an anchor wire is anchored in the tip electrode for mounting the temperature sensors.

In an alternative embodiment, as shown in FIG. 5, an anchor wire 80, which is not used as a puller wire, is provided to locate the temperature sensors within the blind hole 35 of the tip electrode 36. The anchor wire 80 preferably has a diameter of from about 0.20 inch to about 0.27 inch. If desired, the anchor wire 80 may have a smaller diameter and a ferrule, as described above, can be crimped on the outside of the anchor wire to increase the surface area of the anchor wire. The anchor wire 80 has a length preferably slightly longer (e.g., 1 mm to 2 mm) than the length of the blind hole 35 of the tip electrode 36.

As described above with respect to the ferrule 34 on the distal end of the puller wire 42, at least two temperature sensors are mounted along the length of the anchor wire 80. In the embodiment illustrated in FIG. 5, three thermocouples 46 are mounted along the length of the anchor wire 80. The anchor wire 80 is then soldered into the blind hole 35 of the tip electrode 36, preferably along the entire length of the blind hole in a manner similar to that described above.

Figure 6:
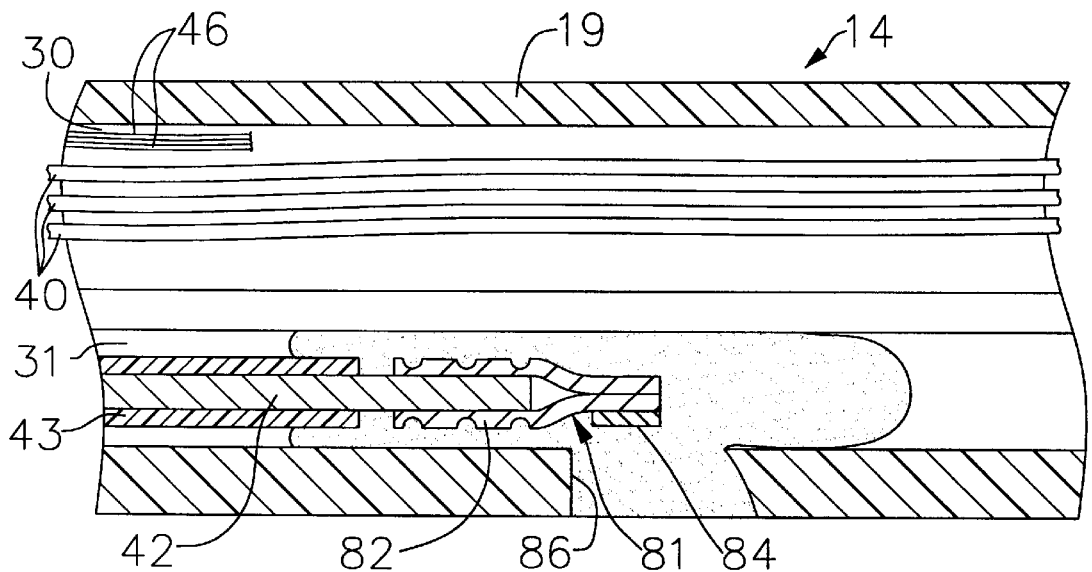
FIG. 6 is a side cross-sectional view of a tip section where the puller wire is anchored to the side of the tubing.
Figure 7:
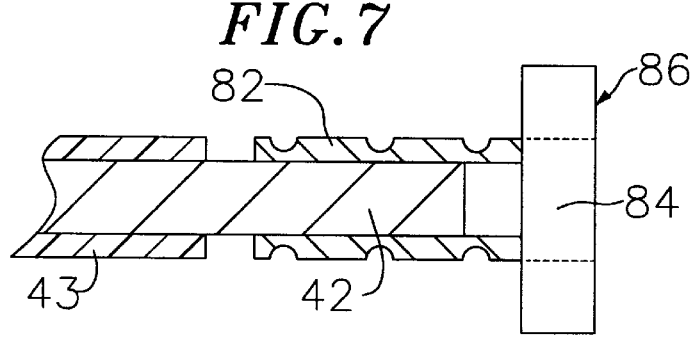
FIG. 7 is a top cross-sectional view of the puller wire anchor of the embodiment of FIG. 6.
Figure 8:
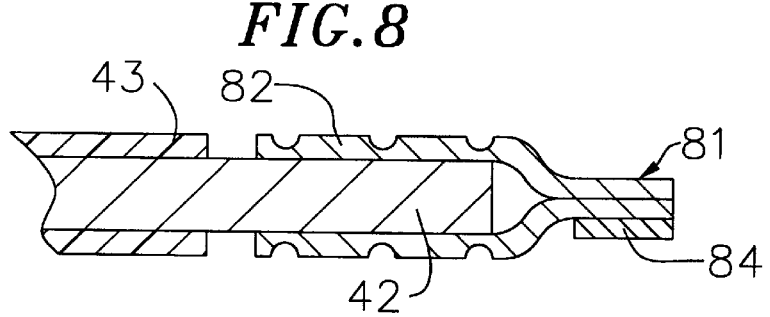
FIG. 8 is a side cross-sectional view the puller wire anchor of the embodiment of FIG. 6.

In this embodiment, the puller wire 42 is anchored to the side of the tip section 14 rather than in the tip electrode 36. A preferred means for anchoring the puller wire 42 to the side of the tip section 14 is shown in FIGS. 6 to 8. An anchor is formed by a metal tube 82, e.g., a short segment of hypodermic stock, that is fixedly attached, e.g., by crimping, to the distal end of the puller wire 42. The tube 82 has a section that extends a short distance beyond the distal end of the puller wire 42. A cross-piece 84 made of a small section of stainless steel ribbon or the like is soldered or welded in a transverse arrangement to the distal end of the tube 82, which is flattened during the operation. This creates a T-bar anchor 81. A notch 86 is created in the side of the tip section 14 resulting in an opening into the second tip lumen 31 carrying the puller wire 42. The T-bar anchor 81 lies within the notch 86. Because the length of the ribbon forming the cross-piece 84 is longer than the diameter of the opening into the second tip lumen 31, the anchor 81 cannot be pulled completely into the second tip lumen 31. The notch 86 is then sealed with polyurethane or the like to give a smooth outer surface.

In another embodiment in accordance with the present invention, there is provided an infusion tube 88 for infusing fluids, including drugs and saline. The infusion tube 88 may also be used for collecting tissue or fluid samples. The infusion tube 88 may be made of any suitable material, and is preferably made of polyimide tubing.

Figure 9:
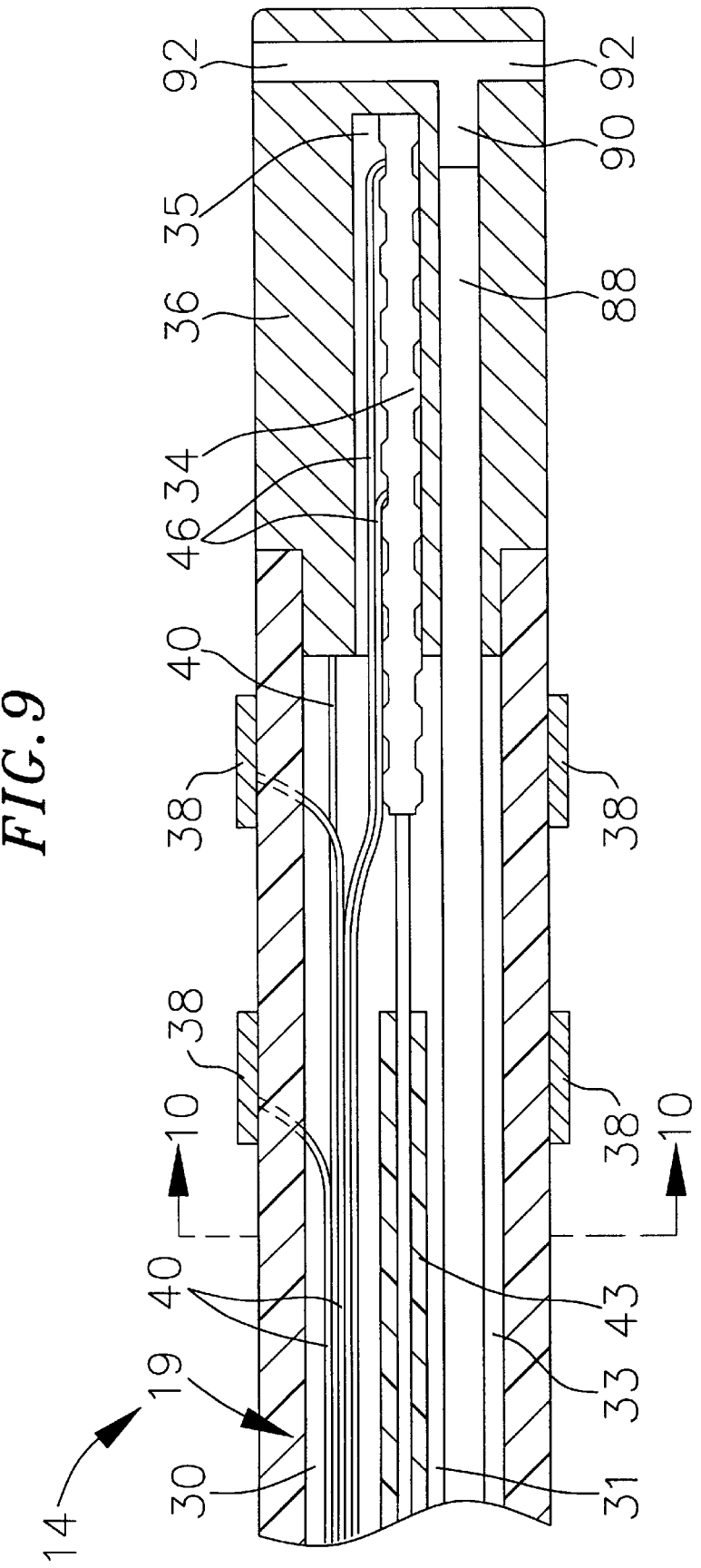
FIG. 9 is a side cross-sectional view of the tip section showing an embodiment having an infusion tube.

With reference to FIGS. 9 and 10, there is shown an alternative embodiment of a catheter according to the invention having an infusion tube 88. The catheter 88 comprises a single lumen catheter body 12 as described above and a tip section 14 comprising three tip lumens 30, 31 and 33. Preferably the first tip lumen 30 and second tip lumen 31 are similar in size, having a diameter of about 0.20 inch, and the third tip lumen 33 is slightly larger, having a diameter of about 0.35 inch.

The infusion tube 88 extends through the catheter body 12 and into the third tip lumen 33. The distal end of the infusion tube 88 extends into a passage 90 through the tip electrode 36, which is different from the blind hole 35. The infusion tube 88 is fixed, e.g., by glue, to the inside of the tip electrode 36. The passage 90 in the tip electrode 36 may be straight or branched as desired. The passage 90 terminates in one or more radial or transverse holes 92 in the tip electrode 36 through which fluids can pass. The transverse holes 92 extend from the passage to the circumference of the tip electrode 36. Preferably the transverse holes 92 are near the distal end of the tip electrode 36. Any other design that allows fluids to flow from the passage into the heart, i.e., a porous tip electrode or a passage that extends out the distal end of the tip electrode, is also included within the scope of the invention.

The proximal end of the infusion tube 88 extends out of a sealed opening in the side wall of the catheter body 12 and terminates in a luer hub or the like. Alternatively, the infusion tube 88 may extend through the control handle 16 and terminate in a luer hub or the like at a location proximal to the control handle.

In an alternative embodiment, the infusion tube 88 extends only through the passage 90 in the tip electrode 36 and the distal end of the third lumen 33. A second infusion tube 89 then extends from the proximal end of the third lumen 33 and through the catheter body 12, and exits the catheter either through the side of the catheter body or out the proximal end of the control handle 16.

As discussed above, preferably the blind hole 35 is an axial blind hole, i.e., extends along the axis of the tip electrode 36. This reduces the risk of erroneous temperature readings, for example, if the temperature sensors are located opposite the side of the tip electrode 36 that is in contact with the heart tissue.

In some circumstances, however, it is preferred that the blind hole 35 extends off-axis. For example, an electromagnetic sensor can be mounted within the tip section 14. An electromagnetic sensor allows a physician to create a visual representation of the heart chamber and to view the location of the sensor, and therefore the catheter tip, within the chamber. A catheter incorporating an electromagnetic sensor is described, for example, in U.S. Patent application Ser. No. 08/924,623, the disclosure of which is incorporated herein by reference. Suitable electromagnetic sensor for use with the present invention are described, for example, in U.S. Pat. Nos. 5,558,091, 5,443,489, 5,480,422, 5,546,951, and 5,568,809 and International Publication Nos. WO 97/36143, WO 97/32179, WO 97/29710, WO 97/29709, WO 97/29701, WO 97/29685, WO 97/29684, WO 97/29683, WO 97/29678, WO 97/25101, WO 97/24983, WO 97/24981, WO 96/41119, WO 96/39929, WO 96/05768, WO 95/09562, and WO 95/02995, the disclosures of which are incorporated herein by reference. Due to the size of the electromagnetic sensor, however, it is difficult for the puller wire to extend along the axis of the tip section. Thus, when an electromagnetic sensor is used, the puller wire and attached temperature sensors can extend into an off-axis blind hole in the tip electrode. Alternatively, the temperature sensors can be mounted on an anchor wire in an axial blind hole where the anchor wire extends only a short distance into the distal end of the tip section.

In another embodiment constructed in accordance with the present invention, two or more puller wires are provided to enhance the ability to manipulate the tip section. In such an embodiment, a second puller wire and a surrounding second compression coil extend through the catheter body and into an additional off-axis lumen in the tip section. The first puller wire is preferably anchored proximal to the anchor location of the second puller wire. For example, when the first puller wire is anchored within the tip electrode, the second puller wire may be anchored to the wall of the tip section. Suitable designs of catheters having two or more puller wires, including suitable control handles for such embodiments, are described, for example, in U.S. Patent application Ser. No. 08/924,342, the disclosure of which is incorporated herein by reference.

For that design and other designs where multiple puller wires are used, the tip electrode has a blind hole for each puller wire that extends into the tip electrode. Two or more temperature sensors are mounted on each puller wire that extends into the tip electrode. For example, if four puller wires are mounted the tip electrode, four blind holes are provided in the four quadrants of the tip electrode. Temperature measurements can then be taken at different locations near the edge of the tip electrode rather than along the axis.

Of course, as would be recognized by one skilled in the art, the present invention can be used in non-steerable catheters. For example, an anchor wire with multiple temperature sensors is mounted within a blind hole in the tip electrode and no puller wire is necessary.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

We claim:

1. A catheter comprising:
   a catheter body having proximal and distal ends and at least one lumen extending therethrough;
   a control handle at the proximal end of the catheter body;
   a tip section having proximal and distal ends and at least one lumen therethrough, the proximal end of the tip section being fixedly attached to the distal end of the catheter body;
   a tip electrode fixedly attached at the distal end of the tip section, the tip electrode having a blind hole in communication with a lumen in the tip section; and
   a wire having proximal and distal ends and extending into the blind hole of the tip electrode, wherein at least two temperature sensors are fixedly attached along a length of the wire.

2. A catheter according to claim 1, wherein two temperature sensors are fixedly attached along the length of the wire.

3. A catheter according to claim 2, wherein the distance between the temperature sensors is from about 40 percent to about 60 percent of a length of the blind hole.

4. A catheter according to claim 2, wherein the distance between the temperature sensors is about 50 percent of a length of the blind hole.

5. A catheter according to claim 2, wherein each of the temperature sensors comprises a thermocouple.

6. A catheter according to claim 1, wherein more than two temperature sensors are fixedly attached along the length of the wire.

7. A catheter according to claim 6, wherein the temperature sensors are equally spaced along the length of the wire.

8. A catheter according to claim 6, wherein each of the temperature sensors comprises a thermocouple.

9. A catheter according to claim 1, wherein at least one of the temperature sensors comprises a thermocouple.

10. A catheter according to claim 9, wherein the thermocouple comprises a double-stranded enameled wire pair comprising a copper wire and a constantan wire.

11. A catheter according to claim 1, wherein the blind hole is an axial blind hole.

12. A catheter according to claim 1, wherein the wire is a puller wire having proximal and distal ends, and wherein the puller wire extends through a lumen in the tip section and through the control handle, and is anchored at its proximal end in the control handle, whereby manipulation of the control handle results in lengthwise movement of the puller wire relative to the catheter body and deflection of the tip section.

13. A catheter according to claim 12, wherein the puller wire comprises a ferrule fixedly attached at its distal end.

14. A catheter according to claim 13, wherein two temperature sensors are fixedly attached along a length of the ferrule.

15. A catheter according to claim 14, wherein the distance between the temperature sensors is about 40 percent to about 60 percent of a length of the blind hole.

16. A catheter according to claim 14, wherein the distance between the temperature sensors is about 50 percent of a length of the blind hole.

17. A catheter according to claim 14, wherein each of the temperature sensors comprises a thermocouple.

18. A catheter according to claim 13, wherein more than two temperature sensors are fixedly attached along a length of the ferrule.

19. A catheter according to claim 18, wherein the temperature sensors are equally spaced along the length of the wire.

20. A catheter according to claim 18, wherein each of the temperature sensors comprises a thermocouple.

21. A catheter according to claim 12, wherein at least one of the temperature sensors comprises a thermocouple.

22. A catheter according to claim 21, wherein the thermocouple comprises a double-stranded enameled wire pair comprising a copper wire and a constantan wire.

23. A catheter according to claim 12, wherein the puller wire comprises a metal ferrule crimped onto its distal end.

24. A catheter according to claim 12, wherein the blind hole is an axial blind hole.

25. A catheter according to claim 1, further comprising a puller wire having proximal and distal ends, wherein the puller wire is anchored in the tip section, extends through a lumen in the tip section and through the control handle, and is anchored at its proximal end in the control handle.

26. A catheter according to claim 1, wherein the tip electrode comprises a passage extending therethrough and where the catheter further comprises an infusion tube extending from a lumen in the tip section into a passage in the tip electrode.

27. A catheter according to claim 26, wherein the tip electrode contains at least one circumferential hole in communication with the passage.

* * * * *